United States Patent [19]

Bucalo

[11] 4,058,116
[45] Nov. 15, 1977

[54] METHODS, MATERIALS, AND DEVICES FOR PROVIDING ELECTRICAL CONDUCTIVITY PARTICULARLY FOR LIVING BEINGS

[76] Inventor: Louis Bucalo, 155 Roberts St., Holbrook, N.Y. 11741

[21] Appl. No.: 641,494

[22] Filed: Dec. 17, 1975

Related U.S. Application Data

[62] Division of Ser. No. 513,295, Oct. 9, 1974, Pat. No. 4,005,699.

[51] Int. Cl.² .............................................. A61B 5/04
[52] U.S. Cl. .................................. 128/2.1 E; 128/418
[58] Field of Search ........... 128/1 R, 1.3, 2 E, 2.06 E, 128/2.06 R, 2.1 E, 2.1 R, 303.1, 362, 404, 407, 416, 417, 418, 419 R, DIG. 4; 106/1; 427/2, 47, 71, 12, 58, 73, 88, 98, 123, 127, 132, 191

[56] References Cited

U.S. PATENT DOCUMENTS

| | | | |
|---|---|---|---|
| 2,555,037 | 5/1951 | Jenson | 128/2.06 E |
| 3,078,850 | 2/1963 | Schein et al. | 128/2.1 E |
| 3,426,746 | 2/1969 | Seamans, Jr. | 128/2.06 E |
| 3,722,005 | 3/1973 | Cowland | 128/2.1 E |
| 3,750,243 | 8/1973 | Prentice | 427/47 |
| 3,769,086 | 10/1973 | Schladitz | 427/58 |
| 3,774,592 | 11/1973 | Lahr | 128/2.1 E |
| 3,791,864 | 2/1974 | Steingroever | 427/47 |

OTHER PUBLICATIONS

"Journal of the American Medical Association", vol. 208, No. 5, May 5, 1969, p. 781.

*Primary Examiner*—William E. Kamm
*Attorney, Agent, or Firm*—Steinberg & Blake

[57] ABSTRACT

Methods and devices for purposes such as nerve stimulation, according to which bodies suspended in a viscous substance are electrically conductive and engage each other so that when injected into a body they will form a reliable electrical path to a nerve, for example.

17 Claims, 5 Drawing Figures

METHODS, MATERIALS, AND DEVICES FOR PROVIDING ELECTRICAL CONDUCTIVITY PARTICULARLY FOR LIVING BEINGS

CROSS REFERENCE TO RELATED APPLICATION

This application is a division of copending application Ser. No. 513,295, filed Oct. 9, 1974, now U.S. Pat. No. 4,005,699, and entitled METHODS, MATERIALS AND DEVICES FOR TREATMENTS SUCH AS ENLARGING TISSUE, FOR PROVIDING ELECTRICAL CONDUCTIVITY, AND FOR STIMULATION AND CONTROL OF BODY FUNCTIONS.

BACKGROUND OF THE INVENTION

The present invention relates to methods, materials and devices to be used for purposes such as providing for living beings treatments involving electrical conductivity in connection with testing, stimulating, or the like.

It is known that for many different purposes it is desirable to conduct electrical energy from an external source to a part of a living being such as a nerve, for example. However up to the present time efficient transmission of electrical energy for this purpose has been unsatisfactory because of the fact that the electrical energy becomes dissipated in the tissue before reaching the desired location unless conductors are implanted surgically with the associated trauma and damage.

Thus, in connection with conducting electrical energy without surgery to an interior body part such as a nerve, for example, at the present time an estimate is made of the best location for an electrode to be placed in engagement with the exterior of the body, and then electrical energy is transmitted by way of the electrode, but becomes rapidly dissipated to a large extent in body tissue before reaching the desired location.

SUMMARY OF THE INVENTION

It is accordingly a primary object of the present invention to provide methods, materials, and devices for avoiding the above drawbacks.

Thus, it is an object of the present invention to provide methods and materials suitable for efficiently conducting electricity to a predetermined part such as a nerve without the use of damaging surgical procedures.

Also, it is an object of the present invention to provide a highly conductive paint.

In accordance with the invention, there is introduced into the tissue a viscous substance which has a plurality of electrically conductive bodies suspended therein and distributed therethrough. By way of such electrically conductive bodies it is possible to conduct electricity efficiently through tissue of a living being.

BRIEF DESCRIPTION OF DRAWINGS

The invention is illustrated by way of example in the accompanying drawings which form part of this application and in which.

DESCRIPTION OF PREFERRED EMBODIMENTS

Figure 1:
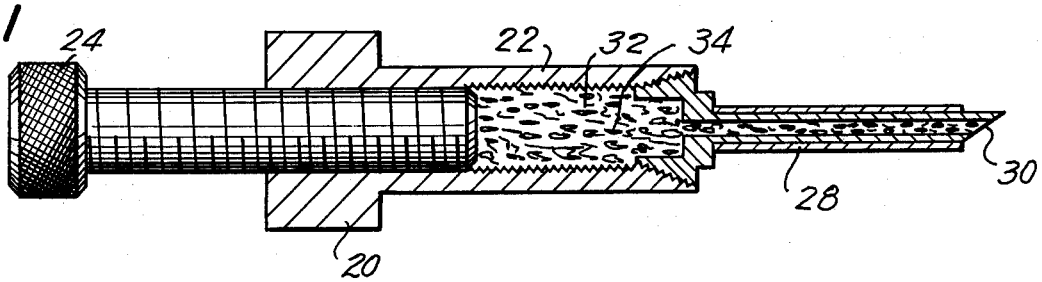
FIG. 1 is a fragmentary partly sectional schematic illustration of a syringe containing materials according to the invention which are introduced into tissue according to the method of the invention.

For the purposes of the present invention, use is made of a syringe 20 as shown in FIG. 1, the syringe 20 having a hollow barrel 22 which receives a screw plunger 24. The outlet of the barrel 22 is connected to a needle 28 the tip 30 of which is introduced into the tissue at the part thereof which is to receive materials of the invention, namely the materials 32 and 34 shown within the barrel 22 in FIG. 1. The material 32 may be in the form of a hydrogenated vegetable oil while the bodies 34 are electrically conductive.

As has been indicated above, it is desirable under some circumstances to transmit electrical energy to certain parts of the body. For example it is well known that certain therapeutic procedures require transmission of electrical energy to a nerve. As the present time in order to carry out procedures of this latter type an approximation is made of the location of the exterior surface of a living being which is closest to the nerve or the like to which electrical energy is to be transmitted, and then an electrode is placed in engagement with the skin at the estimated location for transmitting electrical energy through the tissue to the nerve or the like. However, the result is that a considerable amount of the electrical energy is undesirably and inefficiently dissipated through the body tissue before reaching the desired location such as a nerve or the like. Alternatively, wires are implanted surgically in order to improve procedures of this type.

Figure 2:
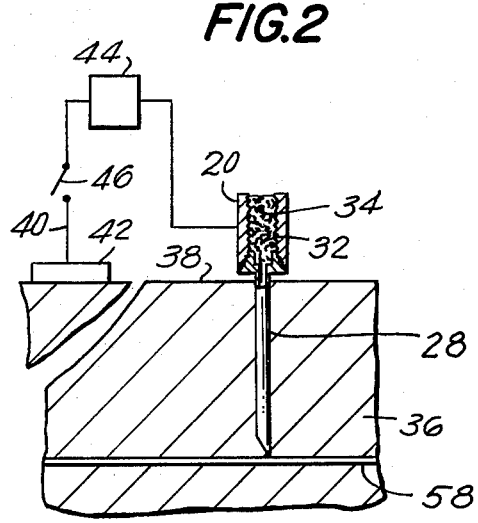
FIG. 2 is a schematic illustration of part of a method of the invention used in connection with rendering a tissue pathway electrically conductive.
Figure 3:
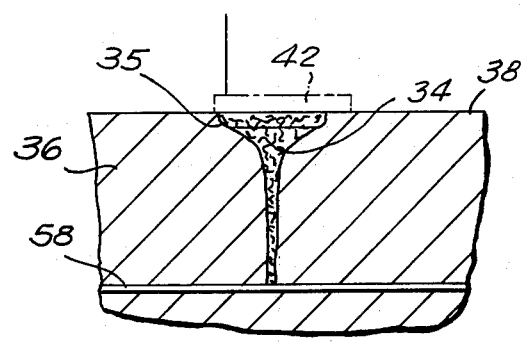
FIG. 3 is a schematic illustration of materials situated in tissue for rendering a pathway in the latter electrically conductive.

The present invention provides the method and materials illustrated schematically in FIGS. 2 and 3. Thus, FIGS. 2 and 3 show fragmentarily in a schematic manner tissue 36 situated beneath the skin 38 which is at the exterior of the body, this tissue 36 having embedded therein a nerve 58.

According to the invention, the syringe 20 has a metallic needle 28, which is electrically conductive internally and preferably insulated externally. For the purposes shown in FIGS. 2 and 3, the substance 32 may be hydrogenated vegetable oil while the bodies 34 are in the form of elongated elecrically conductive particles, made of any conductor such as gold or platinum, these bodies being suspended in the substance 32 in a concentration sufficient to assure that the bodies are distributed throughout the substance 32 and engage each other. It is most preferable, however, to use magnetic bodies 34. With the syringe 20 thus provided with a quantity of the substance 32 with the bodies 34 suspended therein, the needle 28 is introduced into the tissue 36, hopefully in a proper position for engaging the nerve 58, as shown in FIG. 2. In order to check the location of the needle 28, it is located in an electrical circuit 40 having an electrode 42 placed in engagement with the skin 38 as well as a source of electrical stimulation 44 and a switch 46. First the switch 46 is closed so as to complete the circuit, and apply the stimulus and the physician will check as to whether the desired effect is achieved. It the desired effect is not achieved, the physician knows that the needle 28 has not been properly located and will remove the needle and relocate it. When the desired effect is achieved upon closing the switch 46, the physician knows that the needle 28 has been properly situated, and then the needle 28 is withdrawn while the plunger 24 is turned into the barrel 22 so as to leave in the tissue 36 a quantity of the substance 32, as shown schematically in FIG. 3, having the elecrically conductive bodies 34 distributed therethrough. As was indicated above, it is preferred to use for the substance 32 an absorbable medium which will be replaced by tissue 36 which grows into the spaces between and engages the bodies 34. Also, by using magnetic bodies 34 (e.g. any magnetic materials covered with gold or compatible magnetic materials such as a platinum-cobalt alloy), they can be converted into permanent magnets after injection, by placing a suitable strong magnet adjacent the injection, and then the magnetized particles attract and press against each other to provide a highly effective electrically conductive path of low resistance. With the living being treated in the manner shown in FIG. 3. the physician can always locate by x-ray where the bodies 34 are located in the tissue 36, or, if preferred, a suitable permanent mark may be made at the skin 38 to indicate the location of the bodies 34. Thereafter whenever it is desired to transmit electrical energy to this predetermined part of the body, such as the nerve 58, an electrode 42 attached to a stimulator is placed in engagement with the skin 38 in line with the bodies 34 so that the electrical energy is transmitted directly through the bodies 34 to the nerve 58 without undesirable, inefficient dissipation of the electrical energy through the tissue 37. A combination of electrically conductive bodies injected towards a nerve and magnetic particles 35 injected below and near the skin is very effective for maintaining good electrode contact. Typically, electrodes are held in place over the skin with adhesive tapes in combination with electrode jelly. In practice, the adhesive tape does not provide a normal force perpendicular to the skin and the electrical impedance of the contact varies appreciably particularly with muscular motion. Often the electrode jelly migrates and renders the adhesive ineffective. Thus in FIG. 3, the region of the injected materials 35 may be magnetic particles and the electrode 42 may be a conductive permanent magnet which requires no further electrode attachment means.

Figure 4:
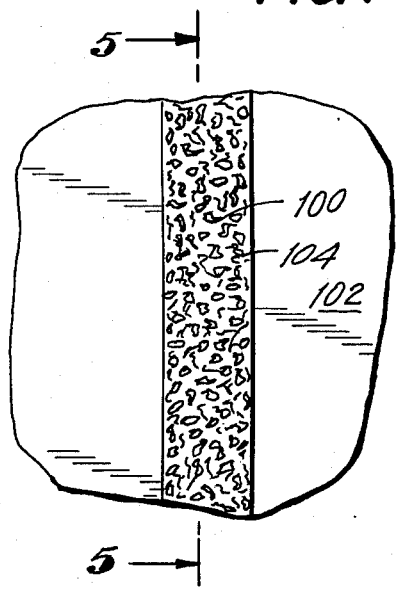
FIG. 4 is a fragmentary schematic plan view of a strip of electrically conductive paint situated on a suitable carrier.
Figure 5:
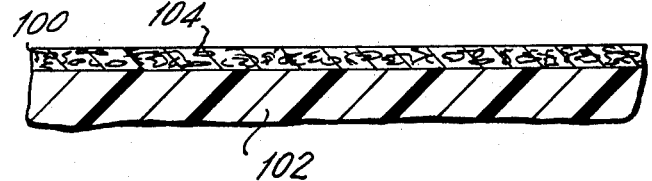
FIG. 5 is a schematic sectional elevation taken along line 5—5 of FIG. 4 in the direction of the arrows.

As has been indicated above in connection with FIG. 3, the conductivity of the body of particles 34 shown in FIG. 3 is increased very greatly by utilizing electrically conductive magnetic particles which attract each other so that as a result of the contact between these particles the resistance is lowered considerably. This principle is of general utility and may be used for purposes such as that illustrated in FIGS. 4 and 5. Thus in connection with strips of paint or plastic which are to be rendered electrically conductive by way of electrically conductive particles carried thereby, considerable problems are encountered in assuring the conductivity of such strips of plastic or paint, this difficulty resulting primarily from the fact that the particles in the liquid can only be maintained reliably in contact with each other by resorting to special measures which create a particular problem in this field. With the arrangement shown in FIGS. 4 and 5, a strip of dried paint or plastic 100 is shown on an electrically conductive base 102. This line of dried liquid 100 has embedded therein electrically conductive particles 104 which are distributed throughout the strip 100 as schematically illustrated. These particles 104 are magnetic as well as electrically conductive. Before the paint or plastic has completely dried the particles 104 are exposed to the influence of a magnetic field which acts on the particles to change them into permanent magnets wich attract each other so that in this way a more reliable contact between the electrically conductive particles is obtained. In this way it is a simple matter to render the liquid carrier electrically conductive so that manufacture of electrical pathways or thick films is considerably simplified.

What is claimed is:

1. In a method of treating a living being, the step of injecting with a syringe, into tissue of the living being, an absorbable viscous substance, in which a plurality of solid bodies are suspended to an extent sufficient to be distributed throughout the viscous substance in an amount sufficient to change the characteristics of the tissue receiving the injection, at least a portion of the bodies being non-absorbable, and at least a portion of the non-absorbable bodies being electrically conductive.

2. In a method as recited in claim 1 and wherein at least a portion of the non-absorbable bodies are elongated fibers.

3. In a method as recited in claim 1 injecting an electrically conducting mass extending from an internal body part to an area within the skin surface to provide a conductive path.

4. In a method as recited in claim 3 and wherein the internal body part includes a nerve.

5. In a method as recited in claim 3 and wherein the syringe has an electrically conductive needle and wherein the conducting path is achieved by initially placing the needle in engagement with the predetermined body part to which electrical energy is to be transmitted, situating the needle in an electrical circuit for varifying the proper location of the needle, and withdrawing the needle from the tissue while simultaneously introducing the viscous substance into the tissue for leaving therein a plurality of the electrically conductive bodies extending from said predetermined part to the region of the exterior skin of the living being for providing efficient transmission of electrical energy to said predetermined part from the skin.

6. In a method as recited in claim 1 and wherein the bodies are magnetic.

7. For use in the treatment of a living being, an absorbable viscous substance having suspended therein a plurality of solid bodies, and a plunger assembly, suitable for connection to an injection needle, enclosing said viscous substance and said solid bodies, at least a portion of said solid bodies being non-absorbable and at least a portion of said non-absorbable bodies being electrically conductive.

8. The combination of claim 7 and wherein said electrically conductive bodies also are magnetizable.

9. The combination of claim 7 and wherein said electrically conductive bodies are suitable for injection into the human body.

10. For use in the treatment of a living being, an absorbable viscous substance having suspended therein a plurality of solid bodies, and a plunger assembly, suitable for connection to an injection needle, enclosing said viscous substance and said solid bodies, an injection needle, and a screw-type fitting, which makes electrical contact to the plunger assembly, joining said injection needle to said plunger assembly, at least a portion of the bodies being non-absorbable, and at least a portion of the non-absorbable bodies being electrically conductive.

11. The combination of claim 10 and wherein said injection needle is electrically conductive internally and electrically insulated externally.

12. In a method for providing an electrically conductive path, the steps of situating a plurality of magnetic electrical particles in a liquid carrier, distributing the liquid carrier along a desired path, magnetizing the particles in the liquid carrier in a manner changing the same into permanent magnets which attract and contact each other, and then permitting the liquid carrier to dry so that the particles remain in the dried carrier rendering the latter conductive.

13. In a method as recited in claim 12 and wherein the carrier is a paint.

14. In a method as recited in claim 12 and wherein the carrier is a plastic.

15. An electrical conductor comprising a body in the form of a dry carrier, and a plurality of electrical particles situated in said body, said particles being permanent magnets which attract and engage each other to provide a path of low electrical resistance.

16. The combination of claim 15 and wherein the carrier is a paint.

17. The combination of claim 15 and wherein the carrier is a plastic.

* * * * *